United States Patent [19]

Gruen et al.

[11] Patent Number: 4,686,979

[45] Date of Patent: Aug. 18, 1987

[54] EXCIMER LASER PHOTOTHERAPY FOR THE DISSOLUTION OF ABNORMAL GROWTH

[75] Inventors: Dieter M. Gruen, Downers Grove; Charles E. Young, Westmont; Michael J. Pellin, Naperville, all of Ill.

[73] Assignee: The United States of America as represented by the United States Department of Energy, Washington, D.C.

[21] Appl. No.: 702,569

[22] Filed: Feb. 19, 1985

Related U.S. Application Data

[63] Continuation-in-part of Ser. No. 569,088, Jan. 9, 1984, abandoned.

[51] Int. Cl.$^4$ .............................................. A61B 17/36
[52] U.S. Cl. .................................................. 128/303.1
[58] Field of Search ............... 128/303.1, 303.14, 395, 128/396, 397, 398

[56] References Cited

U.S. PATENT DOCUMENTS

| | | | |
|---|---|---|---|
| 3,858,577 | 1/1975 | Bass et al. | 128/398 X |
| 4,207,874 | 6/1980 | Choy | 128/303.1 |
| 4,273,109 | 6/1981 | Enderby | 128/303.1 X |
| 4,313,431 | 2/1982 | Frink | 128/303.1 X |
| 4,316,467 | 2/1982 | Mucherheide | 128/303.1 |
| 4,461,283 | 7/1984 | Doi | 128/303.1 X |
| 4,469,098 | 9/1984 | Davi | 128/303.1 |

FOREIGN PATENT DOCUMENTS

WO85/05262 7/1984 PCT Int'l Appl. ............ 128/303.1

OTHER PUBLICATIONS

Gruly, "Artery Zapper", *Discover*, 12-1982, pp. 36-38 & 40.
Doty, "Laser Photocoagulating Dielectric Waveguide Scatpel" IEEE Trans. Biomed. Eng., vol. 28, No. 1, 1-1981, pp. 1-9.
"IBM's Heatless Laser Etching: a Hot IC and Medical Prospect" in *News Spectra*, Jul. 1983.
"Heatless Laser Etching" by John Free in *Popular Science*, Dec. 1983, p. 114.
"Spread of Lasers . . . Spine Straightener . . . Rebuilding Faces" in *U.S. News and World Report*, Oct. 31, 1983.
"Laser Coronary Angioplasty: Experience with 9 Cadaver Hearts", by Daniel S. J. Choy, et al. in *The American Journal of Cardiology*, 50, Dec. 1982, pp. 1209–1211.
"Arterial Response to Laser Operation for Removal of Atheroschlerotic Plaques" by Ross G. Gerrity, et al., in Journal Thorac Cardiovasc. Surg. 85:409–421, 1983.
"Laser-Dissolution of Coronary Atherosclerotic Obstruction" by Garrett Lee, et al., in *American Heart Journal*, Dec. 1981, pp. 1074–1075.
"Feasibility of Intravascular Laser Irradiation for in vivo Visualization and Therapy of Cardiocirculatory Diseases" by Garrett Lee, et al., in *American Heart Journal*, Jun. 1982, pp. 1076–1077.

*Primary Examiner*—Edward M. Coven
*Attorney, Agent, or Firm*—William Lohff; James W. Weinberger; Judson R. Hightower

[57] ABSTRACT

Removal of abnormal human tissue with reduced thermal damage is achieved by selecting a laser having a wavelength in the order of 290–400 nm, orienting a laser-transmitting glass member toward the abnormal tissue and directing the laser through the glass member at power densities, pulse rates, and times sufficient to cause multiphoton absorption and bond breaking by Coulomb repulsion rather than thermal destruction. The glass member may include a laser beam concentrator provided by a lens or cone at the tissue-treatment end to increase the beam energy per unit area and reduce the treatment area.

15 Claims, 6 Drawing Figures

EXCIMER LASER PHOTOTHERAPY FOR THE DISSOLUTION OF ABNORMAL GROWTH

CONTRACTUAL ORIGIN OF THE INVENTION

The U.S. Government has rights in this invention pursuant to Contract No. W-31-109-ENG-38 between the U.S. Department of Energy and the University of Chicago representing Argonne National Laboratory.

This is a continuation-in-part of U.S. application Ser. No. 569,088 filed Jan. 9, 1984, now abandoned.

BACKGROUND OF THE INVENTION

This invention relates to a method and apparatus for the penetration of an abnormal human tissue or other objectionable biological growth, protrusion or obstruction on the surface of or within the human body for surgical purposes and with reduced thermal damage to adjacent normal tissue. More particularly, the invention relates to the removal through the use of a special laser of an abnormal biological growth or obstruction under conditions which reduce thermal and/or acoustic damage to adjacent normal tissue. A special feature of the invention also relates to the concentration of the laser beam and the resulting reduction in the treatment area.

In recent years, lasers have become of importance in microsurgery because of their ability to produce relatively bloodless incisions of great precision. In some instances, laser beams typically Nd-YAG or $CO_2$ with respective wavelengths of 1.06 $\mu$m and 10.6 $\mu$m, have been transmitted through optical wave guides to an abnormal tissue growth or obstruction and used to penetrate and sever the objectionable material from remaining tissue. Typical findings with these lasers have been that significant tissue damage has occurred with the magnitude of injury being proportional to total delivered laser energy. These findings have also indicated that calcified as well as noncalcified plaques were penetrated with similar levels of injury.

One of the major problems with conventional lasers used in this treatment is that the high energies used to remove tissue often cause significant thermal and/or acoustic damage to surrounding tissue. Particularly in the removal of an construction from within a blood vessel, thermal damage may weaken an adjacent wall of the vessel or result in penetration of the wall. Therefore, a new technique for removing human tissue would be desirable.

Accordingly, one object of this invention is the removal of human tissue with a low degree of thermal and/or acoustic damage. Another object is the removal of human tissue with a more effective use of laser energy for the desired incision. These and other objects will become apparent from the following detailed description.

SUMMARY OF THE INVENTION

Briefly, the invention is directed to the removal of abnormal tissue with reduced thermal and/or acoustic damage by selecting a laser differing in wavelength from conventional medical lasers, orienting a laser transmitting glass member toward the abnormal tissue, and directing the laser through the glass member at energy levels, pulse repetition rates and times sufficient to accomplish the removal with reduced damage. The selected laser has a wavelength in the order of 290–400 nm and preferably about 290–320 nm. This laser may be used at power densities in the order of about 0.1–1.0 gigawatt/$cm^2$ to penetrate tissue with a reduced temperature and associated thermal damage to adjacent tissue. Conventional lasers generate a high temperature in tissues which in some instances cause the cells to explode from steam generated from cell water. With the laser of the inventive method and apparatus, multiphoton absorption processes lead to a population of highly excited molecular electronic states and to bond breaking by Coulomb repulsion rather than thermal destruction.

The result is a more effective use of the laser energy in penetrating and severing tissue with reduced thermal effects on surrounding tissue. The laser has a wavelength in the range of about 290–400 nm and preferably about 290–320 to be capable of being transmitted through a glass member which may be used for transmission and/or focusing of the laser beam. Preferably, the glass member is flexible and may be inserted into a blood vessel and positioned adjacent the obstruction. Positioning may be accomplished by the glass member having a visible light outer layer for transmitting a visible image of the vessel and obstruction.

A further special feature of the invention relates to the optical coupling of a beam concentrator to the treatment end of the glass member to provide an increase in beam energy per unit area and reduce the area for treatment. The resulting combination of properties is particularly useful in the use of the fiber-directed laser for eye surgery where a high degree of precision and an increase in beam energy are important.

DETAILED DESCRIPTION OF THE PREFERRED EMBODIMENT

The inventive method of severing a human tissue comprises the steps of providing a laser-transmitting member composed of glass, exposing at least a portion of the tissue to the laser transmitting member, and directing a laser beam having a wavelength of about 290–400 nm through the laser-transmitting member to the tissue for a time sufficient to penetrate the tissue and sever the tissue portion from the remaining tissue.

The laser beam is further characterized by laser pulses of 3–20 ns and preferably about 8 ns with up to 60 mJ energy at rates up to about 0 to ~200 Hz duration and preferably about 130 Hz, corresponding to 8 MW peak and 8 W average power. Higher pulse repetition rates up to about 300 Hz are possible with reduced pulse energy, the average power remaining approximately constant. With the above pulse times, the conversion of laser photon energy to vibrational and ultimately lattice photon energy occurs on a more rapid time scale compared to that for the laser pulse. Typically, the conversion is in the order of $10^{-11}$ to $10^{-12}$ seconds compared to the $10^{-8}$ second laser pulse.

The laser-transmitting member is composed of glass and may be an elongated optical fiber which preferably is flexible, and/or a focusing lens for directing the laser beam with precision to the specific section of tissue to be severed. Suitable glasses include pure fused silica, and other glasses, e.g., Corning 7910, or 9741 with pure fused silica being preferred. Preferably the glass member is adjustable or may be arranged to provide an accurate focusing and/or positioning of the laser beam with respect to the tissue. It is further preferable that the glass member be movable so that the laser beam may be moved with precision relative to the tissue to provide a linear cutting action.

Particularly where the area of treatment is extremely small and/or where increased levels of beam energy per unit area are required, a beam concentrator may be optically coupled to the treatment end of the glass member. Suitably, the concentrator includes a focusing lens, a conical member or the like.

Figure 1:
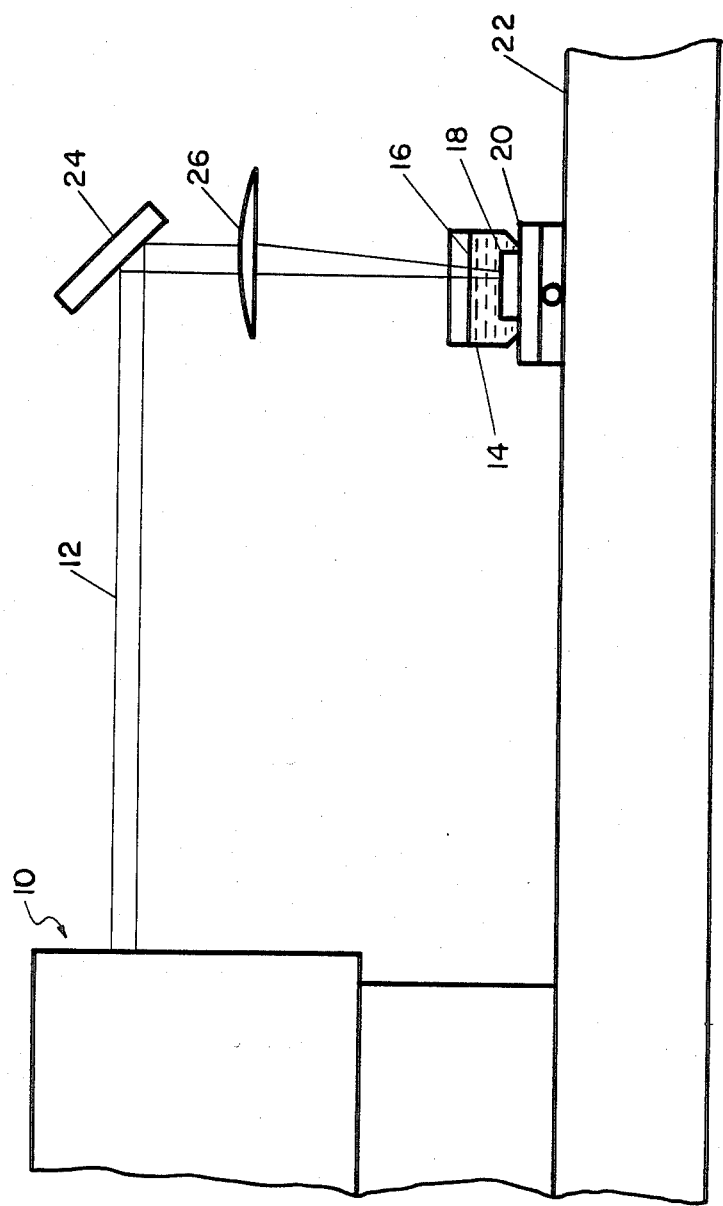
FIG. 1 is a schematic drawing of the apparatus representing one embodiment of this invention.

One embodiment of the invention is illustrated in FIG. 1. An excimer laser 10 provides a beam 12 to produce incisions in a tissue sample 18. As illustrated, beam 12 is directed through a saline solution 16 in beaker 14 on adjustable base 20. An optical table 22 provides a common support for both the excimer laser 10 and base 20. Mirror 24 provides a change in direction of beam 12 which is then focused by glass lens 26.

Figure 2:
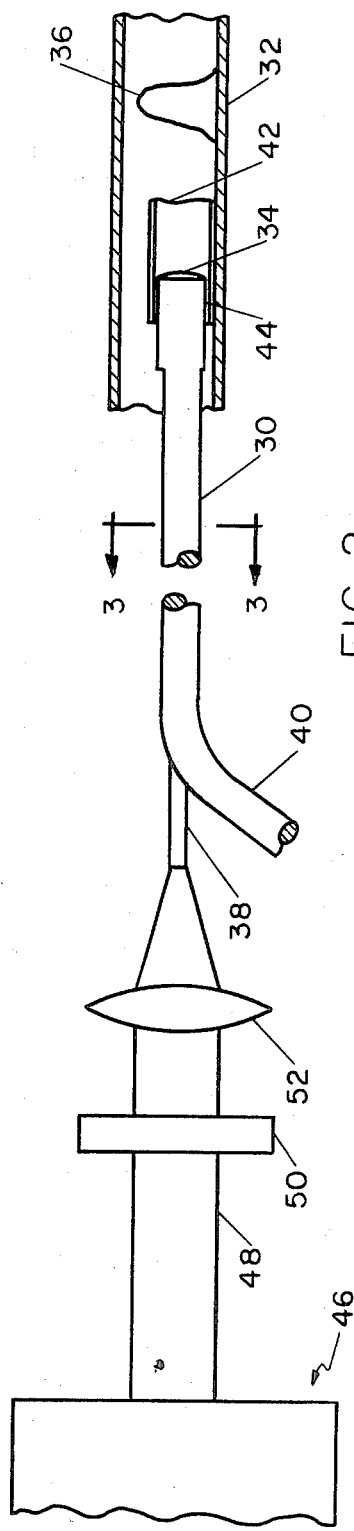
FIG. 2 is an enlarged, simplified representation of the insertion of an optical fiber into a blood vessel.
Figure 3:
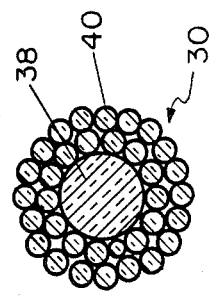
FIG. 3 is an enlarged sectional view of the optical fiber of FIG. 2 taken along line 3—3 to illustrate the core and surrounding optical fibers.

The inventive method and apparatus are particularly useful for removing internal obstructions within blood vessels by severing at least a portion of the obstruction by action of the laser through the glass member. As illustrated in FIGS. 2-3, the flexible glass member 30 is inserted into a blood vessel 32 which has been bypassed with respect to normal blood circulation. The glass member 30 is positioned so that its forward face 34 is adjacent, and aimed at obstruction 36 which may represent a deposit or growth causing partial blockage in the blood vessel 32. Preferably, glass member 30 has a laser transmitting core 38 surrounded by a plurality of glass fibers 40 surrounding to provide a visible image of the interior of vessel 32 including the obstruction 36 at an external image display. As illustrated, fibers 40 are flexible and may be separated from core 38 for connection to a display. An outer cover, as partially illustrated by cover 42, is provided to form a passage 44 by which particles of the biological growth or deposit may be removed by vacuum during the operation.

An excimer laser 46 provides a laser beam 48 which is focused by glass lens 50 and 52 and transmitted through core 38 of glass member 30. When the glass member has been accurately located, the laser beam is directed at the growth for a time sufficient to sever a portion of the growth from remaining tissue. The time will vary depending on a variety of conditions but generally is in the order of about one minute. The laser has a wavelength of about 290-400 nm which essentially covers the useful range with respect to glass transmission. Lasers of low wavelengths may provide the desired photochemical bond repulsion with respect to some plastic compositions, but do not transmit through glass. Lasers with higher wavelengths may transmit through glass but do not provide the desired repulsion of the near UV laser. Accordingly, lasers of 290-400 nm not only are capable of being transmitted through glass but also of developing low thermal damage to human tissues. The performance is somewhat surprising since results from the 290-400 nm laser on human tissue would not be predictable. A further advantage of an excimer operation at 290-400 nm and preferably 290-320 nm over the use of lower wavelength lasers (i.e., 193 nm) is that at comparable energies per pulse, the higher wavelength lasers of 290-400 nm provide a greater number of pulses by a factor of at least about 30 before depletion to half-power.

Figure 4:
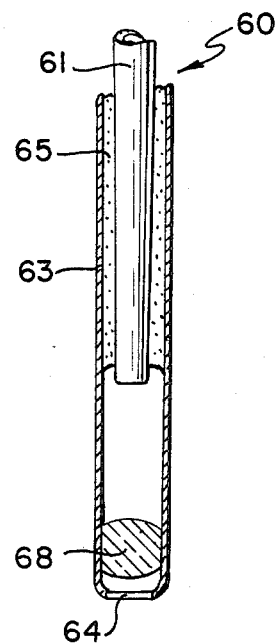
FIG. 4 is an enlarged, simplified side view of an optical fiber being utilized in the invention with a beam concentrator.
Figure 5:
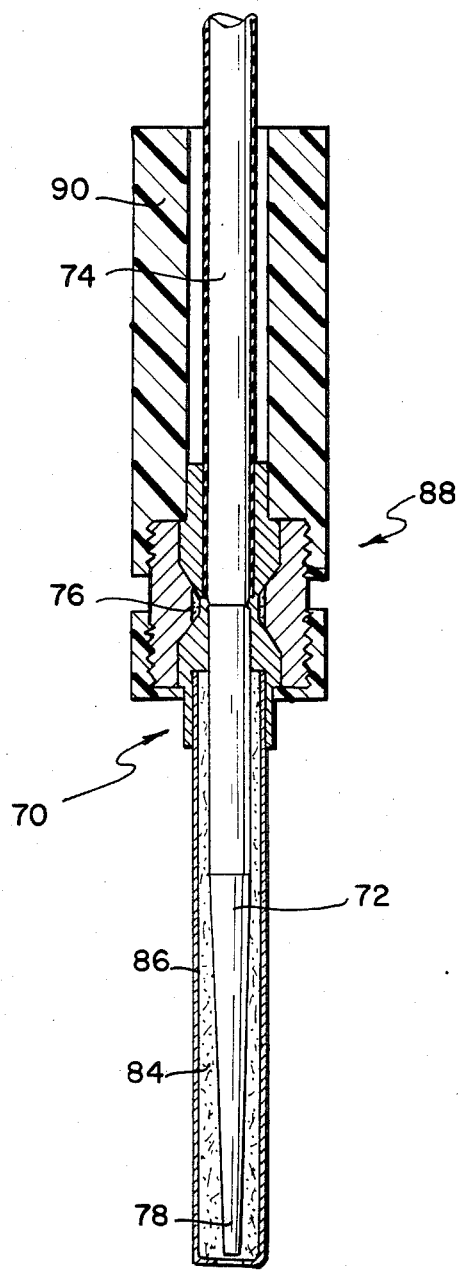
FIG. 5 is a similar view as FIG. 4 with a second beam concentrator.
Figure 6:
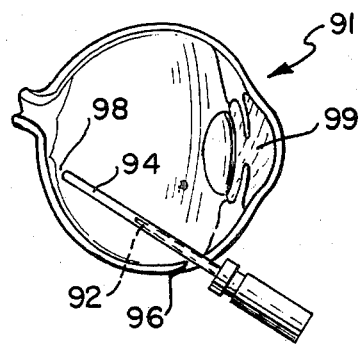
FIG. 6 is a reduced view of apparatus of the general type illustrated in FIG. 5 inserted in an eye of an animal for treating an abnormal tissue.

Particularly where eye or other surgery is to be carried out on an extremely small area with high precision, the laser beam is concentrated as illustrated in FIGS. 4-5. This is also useful for increasing the beam energy per unit area where increased levels of beam energy are required. As illustrated in FIG. 4, the laser transmitting member 60 for the laser beam (not shown) has an opposite end section 64 for positioning adjacent the tissue portion (not shown). End section 64 includes lens 68 to provide the desired concentration achieved by focusing of the beam. Laser transmitting member 60 further includes glass section 61 held within metal shield 63 by sealant 65 and optically coupled to lens 68. As illustrated, metal shield 63 retains glass section 61 and lens 68 in axial alignment. In FIG. 5, the beam concentrator is illustrated as a conical glass member 72 coupled to section 74 of the glass member 70 by a coupling fluid 76. Small end 78 of the cone 72 is located for positioning adjacent the tissue portion to be treated. Cone 72 is retained by sealant 84 within metal shield 86. Optical and axial alignment of cone 72 and glass member 70 is provided by coupling mechanism 88 which also provides a handle 90. As illustrated in FIG. 6, cone 92 and shield 94 are inserted through outer tissue 96 of an eye 91 and positioned adjacent tissue 98 to be treated with the laser beam. The remaining features of the apparatus are of the type illustrated in FIG. 5. One of the advantages of the use of cone 92 is that the laser beam may be concentrated as it contacts tissue 98 and thereafter will diverge to lessen the effect on tissue below the tissue of primary concern as well as adjacent tissue. The apparatus illustrated in FIG. 6 may be monitored by an optical system (not shown) through the cornea 99 of eye 91.

The following examples are provided for illustrative purposes and are not intended to be restrictive as to the scope of the invention:

EXAMPLE I

The invention was carried out by directing an excimer laser operating in near UV at 308 nm on samples of human aorta as generally illustrated in FIG. 1. The excimer laser was based on a standard Xe/HCl/He mixture. A laser mirror was located to provide a change in direction of the beam with the beam being focused by a 200 mm focal length fused silica lens placed about 1 m from the mirror. The sample was placed at the focus of the lens where the laser energy passed through a 0.5×1.2 mm minimum rectangular area, limited by the divergence of the excimer laser beam.

Laser pulses of 8 ns duration were produced by the excimer laser with measured output energy being about 30 mJ/pulse. The energy per pulse was essentially constant in the 0.1 to 100 Hz repetition rate. Energy was emitted from the laser output mirror in a rectangular mode 8×20 mm, with a corresponding divergence of 2.4×6 mn. Each sample was treated with about 10-100 laser pulses. Visual inspection of the aortic samples irradiated both in air and under saline solution revealed wedge shaped incisions without visual evidence of surrounding thermal damage.

EXAMPLE II

Apparatus of the type illustrated in FIG. 5 was assembled to provide a separate glass member for concentration of the laser beam. The apparatus included a clad optical fiber (UV grade fused silica), a glass cone (of the same composition) optically coupled to fiber by an index matching fluid, a housing holding the fiber and cone in axial alignment and providing a handle, and a metal shield extending along the length of the cone with an opening to expose the small end of the cone. A sealant was also provided between the shield and cone. The reduction in diameter provided by the cone was approximately 1000:300 μm. A test was carried out with the above apparatus wherein the conical end was positioned adjacent retinal tumors of a rabbit by first surgically inserting the conical end through the outer tissue of the eye. The laser described in Example I was utilized at a level estimated to be about 2-5 mj. and the beam was reduced to a smaller area by the cone before contacting the tissue of retina. During the test, use of the cone to concentrate the beam allowed the removal of timer to proceed with a minimum of retinal damage. This improvement over simple fiber surgery arose from two factors. The first is evident from the laser spot size which was decreased by over an order of magnitude. The second arises from depth of focus of the beam. The divergence of the laser from the conic section is very large thus limiting the depth of cutting.

The foregoing description of embodiments of the invention has been presented for purposes of illustration and description. It is not intended to be exhaustive or to limit the invention to the precise form disclosed, and obviously many modifications and variations are possible in light of the above teaching.

The embodiments of the invention in which an exclusive property or privilege is claimed are defined as follows:

1. A method of severing a human tissue comprising the steps of
    providing a laser-transmitting member composed of glass,
    exposing at least a portion of the tissue to the laser transmitting member, and
    directing a laser having a wavelength of about 290-400 through the laser transmitting member to the tissue portion for a time and at an intensity level sufficient to penetrate the tissue and separate a tissue portion from remaining tissue.
2. The method of claim 1 including a step of arranging the laser transmitting member to direct the laser to a predetermined location on the tissue and wherein the step of directing the laser is carried out with a laser having a wavelength of about 290-320 nm and at an intensity level of at least 0.1 gigawatt/cm$^2$.
3. The method of claim 2 wherein the arranging step includes movement of the laser-transmitting member to move the laser beam relative to the tissue.
4. The method of claim 2 wherein the step of providing a laser-transmitting member provides a flexible member.
5. The method of claim 4 wherein the tissue is internally located in the human and the step of exposing the tissue portion includes inserting the flexible laser-transmitting member in the human to a position adjacent the tissue.
6. The method of claim 5 wherein the step of directing the laser beam utilizes a laser beam of about 308 nm.
7. The method of claim 1 wherein the step of providing a laser-transmitting glass member includes providing a laser beam concentrator for concentration of the beam before contact with the tissue.
8. The method of claim 7 wherein the step of providing a laser beam concentrator provides a glass section and a conical member optically coupled to the glass section and having a small end directed at the tissue.
9. Apparatus for severing human tissue comprising
    at least one glass member for transmitting a laser beam arranged to direct a laser beam to the tissue, and
    laser means for providing and directing a laser beam having a wavelength of about 290-400 nm through the glass member to the tissue for a time and at an intensity level suffficient to penetrate the tissue and sever said tissue from remaining tissue.
10. The apparatus of claim 9 wherein said one glass member includes an elongated flexible section for being inserted into a blood vessel containing said tissue, said laser is operated at a wavelength of about 290-320 nm and said intensity level is at least about 0.1 gigawatt/cm$^2$.
11. The apparatus of claim 10 including a second glass member having a lens shape and arranged between the laser means and said flexible section of glass.
12. The apparatus of claim 11 wherein the laser beam has a wavelength of about 308 nm.
13. The apparatus of claim 9 wherein the glass member includes a tissue treatment section and a laser beam concentrator.
14. The apparatus of claim 13 wherein the laser beam concentrator includes a lens.
15. The apparatus of claim 13 wherein the glass member includes a glass section and the laser beam concentrator includes a conical member, optically coupled to the glass section.

* * * * *